United States Patent
Stutts, III et al.

(10) Patent No.: US 6,235,266 B1
(45) Date of Patent: *May 22, 2001

(54) DINUCLEOTIDES USEFUL FOR THE TREATMENT OF LUNG DISEASE

(75) Inventors: Monroe Jackson Stutts, III; Richard C. Boucher, Jr., both of Chapel Hill; Eduardo R. Lazarowski, Durham, all of NC (US); Cara A. Geary, Seattle, WA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/303,491

(22) Filed: Apr. 30, 1999

Related U.S. Application Data

(63) Continuation-in-part of application No. 08/486,988, filed on Jun. 7, 1995, now Pat. No. 5,635,160.

(51) Int. Cl.$^7$ ..................................................... A61K 9/12
(52) U.S. Cl. ............................................. 424/45; 424/489
(58) Field of Search ..................................... 424/489, 464, 424/45, 46

(56) References Cited

U.S. PATENT DOCUMENTS

| | | | |
|---|---|---|---|
| 3,313,813 | 4/1967 | Cragoe | 260/250 |
| 4,501,729 | 2/1985 | Boucher et al. | 424/45 |
| 5,292,498 | 3/1994 | Boucher et al. | 424/45 |
| 5,304,125 | 4/1994 | Leith | 604/57 |

(List continued on next page.)

OTHER PUBLICATIONS

M. Knowles et al.; Activation by Extracellular Nucleotides of Chloride Secretion in the Airway Epithelia of Patients with Cystic Fibrosis; *N. Engl. J. Med.* 325 533–538 (1991).

(List continued on next page.)

*Primary Examiner*—Thurman K. Page
*Assistant Examiner*—R. Joynes
(74) *Attorney, Agent, or Firm*—Myers Bigel Sibley & Sajovec

(57) ABSTRACT

A pharmaceutical formulation comprises, in an amount effective to hydrate lung mucous secretions, a compound of Formula (I):

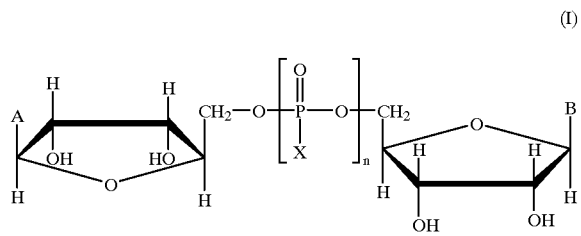

wherein
n is from 1 to 6;
X is —OH or —SH;
A and B are each independently selected from the group consisting of:

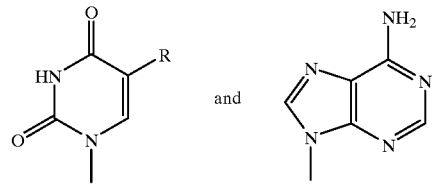

wherein R is H or Br;
or a pharmaceutically acceptable salt thereof, in a pharmaceutically acceptable carrier. A method of hydrating mucous secretions in the lungs of a subject in need of such treatment, comprising administering to the lungs of the subject a compound of Formula I as given above, is also disclosed.

20 Claims, 3 Drawing Sheets

U.S. PATENT DOCUMENTS

| | | |
|---|---|---|
| 5,512,269 | 4/1996 | Molina y Vedia et al. ............ 424/45 |
| 5,628,984 | 5/1997 | Boucher et al. ........................ 424/45 |
| 5,635,160 | 6/1997 | Stutts, III et al. ...................... 424/45 |
| 5,656,256 | 8/1997 | Boucher et al. ........................ 424/45 |
| 5,683,675 | 11/1997 | Molina y Vedia et al. ............ 424/45 |
| 5,725,842 | 3/1998 | Boucher et al. ........................ 424/45 |

OTHER PUBLICATIONS

M. Knowles et al.; Extracellular ATP and UTP Induce Chloride Secretion in Nasal Epithelia of Cystic Fibrosis Patients and Normal Subject in vivo, *Chest* 101:60S–63S (1992).

S. Mason et al.; Regulation of transepithelial ion transport and intracellular calcium by extracellular ATP in human normal and cystic fibrosis airway epithelium, *Br. J. Pharmacol* 103:1649–1656 (1991).

K. Ng et aL.; The action of a water–soluble carbodiimide on adenosine 5'–polyphosphates, *Nucl. Acids Res.* 15:3573–3580 (1987).

M. Stutts et aL.; Multiple modes of regulation of airway epithelial chloride secretion by extracellular ATP, *Am J. Physiol.* 267:C1442–1451 (1994).

DINUCLEOTIDES USEFUL FOR THE TREATMENT OF LUNG DISEASE

RELATED APPLICATIONS

This application is a continuation-in-part of commonly owned, U.S. patent application Ser. No. 08/486,988, filed Jun. 7, 1995, now U.S. Pat. No. 5,635,160 the disclosure of which is incorporated by reference herein in its entirety.

FIELD OF THE INVENTION

This invention relates to certain dinucleotides, pharmaceutical formulations containing the same, and methods of hydrating retained mucous secretions in the lungs of a subject by administering dinucleotides to the subject.

BACKGROUND OF THE INVENTION

In cystic fibrosis several functions of airway epithelia are abnormal, and deficiencies in both $Cl^-$ transport and $Na^+$ absorption are well documented. See, e.g. Knowles et al., *Science* 221, 1067 (1983); Knowles et al., *J. Clin. Invest.* 71, 1410 (1983). Regulation of Lon transport might have potential therapeutic benefit in lung diseases characterized by abnormalities in epithelial ion transport, e.g., cystic fibrosis.

One therapeutic goal in cystic fibrosis and other pulmonary diseases in which the water content of the mucous is altered is to hydrate the lung mucous secretions, so that the secretions may be thereafter more easily removed from the lungs by mucociliary action or simple coughing. The use of aerosolized amiloride to hydrate mucous secretions is described in U.S. Pat. No. 4,501,729. Amiloride appears to block $Na^+$ reabsorption by airway epithelial cells, and therefore inhibits water absorption from the mucous.

A different therapeutic approach for hydrating lung mucous secretions is exemplified by techniques that involve the administration of ATP or UTP, which appear to stimulate chloride secretion from respiratory epithelial cells. See, e.g., U.S. Pat. No. 5,292,498 to Boucher.

In view of the large numbers of people afflicted with cystic fibrosis, there is an ongoing need for new methods for providing methods of hydrating lung mucous secretions and thereby facilitating lung mucous clearance.

SUMMARY OF THE INVENTION

A first aspect of the present invention is a pharmaceutical formulation comprising, in a pharmaceutically acceptable carrier (e.g., a solid or liquid carrier), a compound of Formula (I)

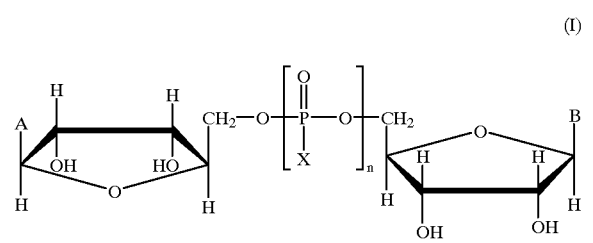

(I)

or a pharmaceutically acceptable salt thereof, in an amount effective to hydrate lung mucous secretions. In a compound of Formula I:

n is from 1 to 6. n is preferably from 2 to 4, and is most preferably 4.

X is —OH or —SH, and is preferably —OH.

A and B are each independently selected from the group consisting of:

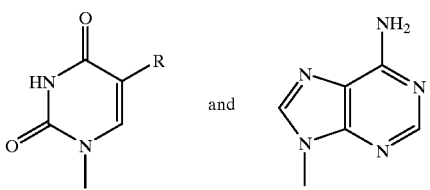

wherein R is H or Br. Optionally, the pharmaceutical formulation may further comprise a compound selected from the group consisting of amiloride, benzamil and phenamil in an amount effective to inhibit the reabsorption of water from lung mucous secretions.

A second aspect of the present invention is a method of hydrating mucous secretions in the lungs of a subject in need of such treatment, comprising administering to the lungs of the subject a compound of Formula I as given above, or a pharmaceutically acceptable salt thereof, in an amount effective to hydrate lung mucous secretions.

A third aspect of the present invention is a method of treating cystic fibrosis in a subject in need of such treatment, comprising administering to the lungs of the subject a compound of Formula I as given above, or a pharmaceutically acceptable salt thereof, in an amount effective to hydrate lung mucous secretions.

A fourth aspect of the present invention is the use of a compound of Formula I as given above, or a pharmaceutically acceptable salt thereof, for the preparation of a medicament for hydrating mucous secretions in the lungs of a subject in need of such treatment.

The foregoing and other objects and aspects of the present invention are explained in detail in the specification set forth below.

DETAILED DESCRIPTION OF THE INVENTION

Figure 1:
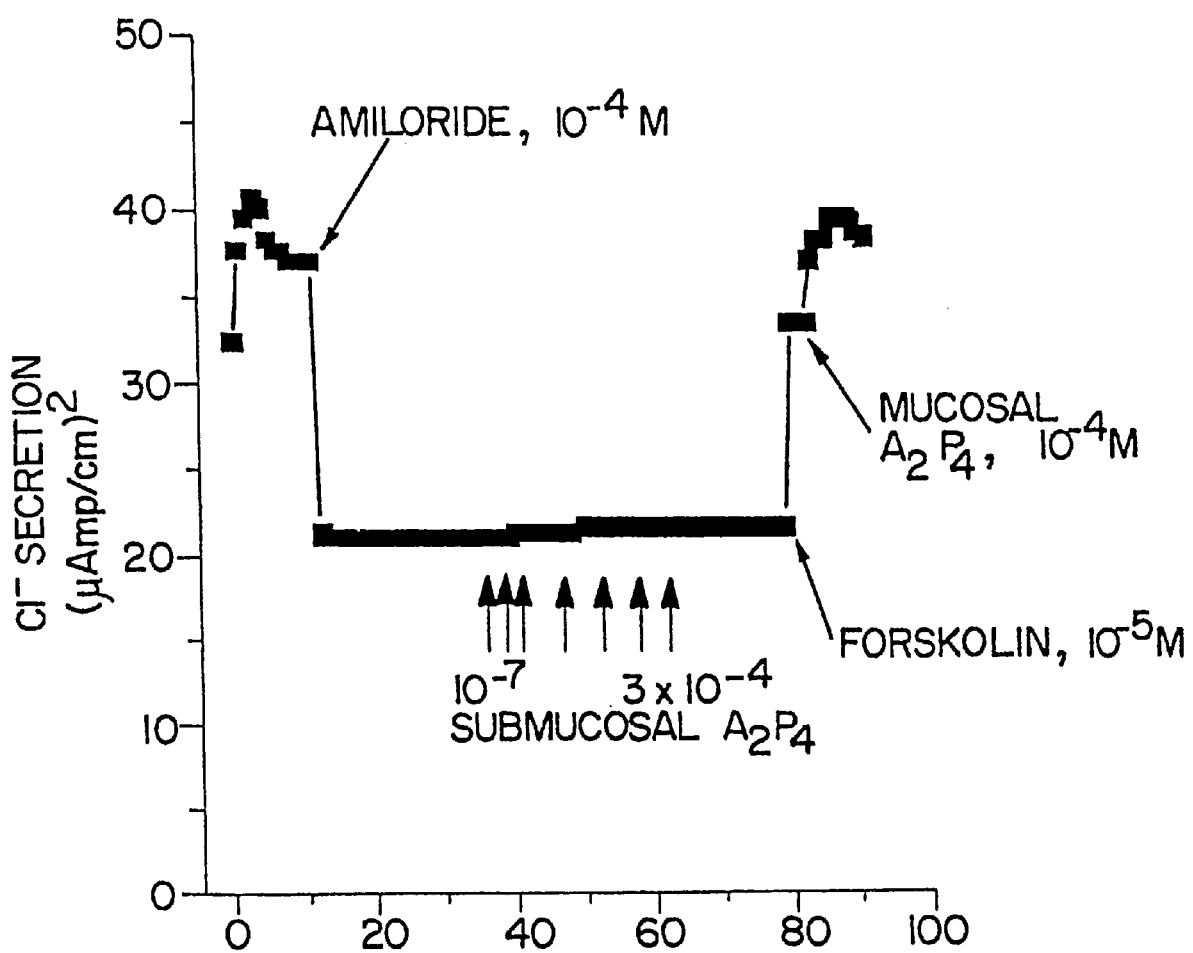
FIG. 1 shows the effect of dinucleotide $A_2P_4$ on $Cl^-$ secretion on the luminal surface of airway epithelia previously treated with forskolin.
Figure 2:
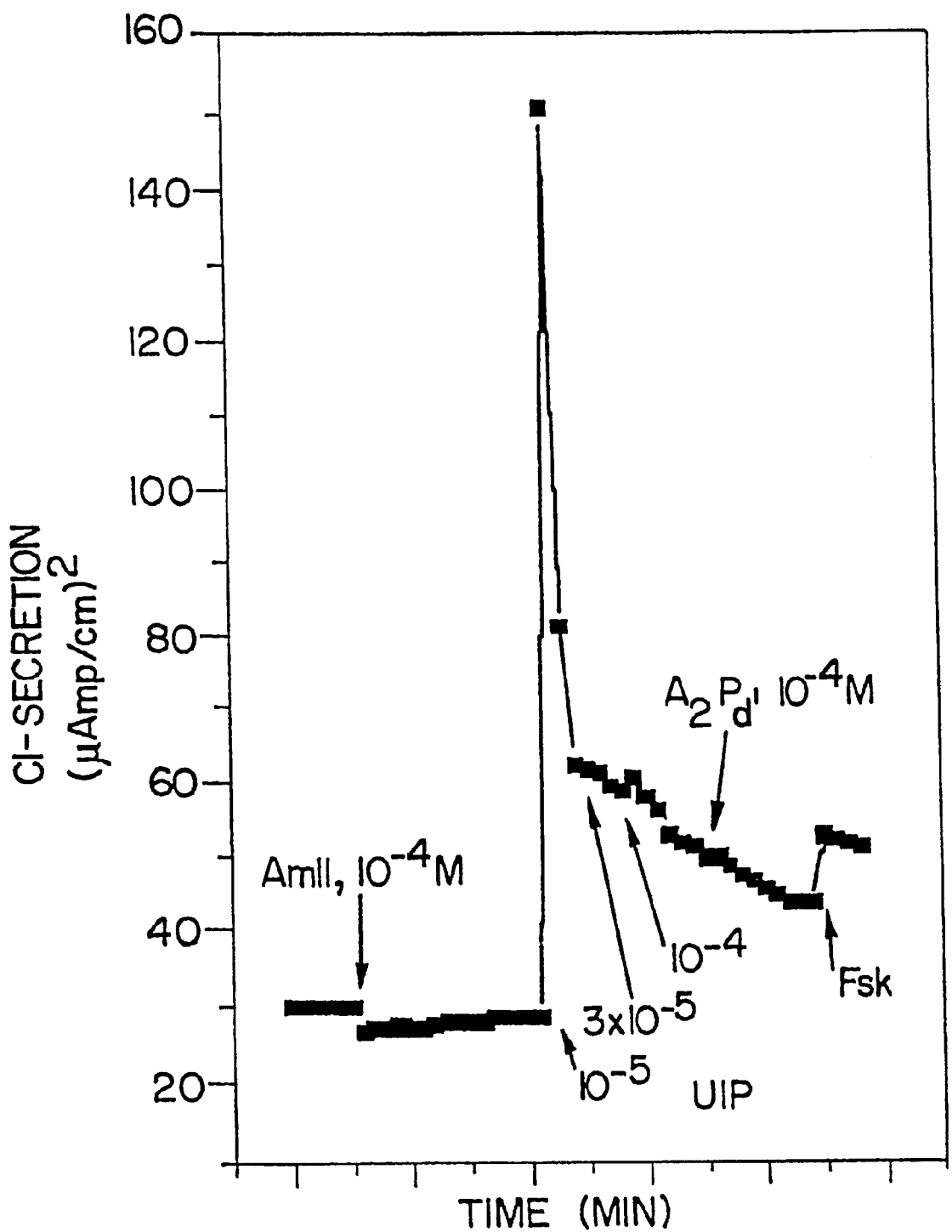
FIG. 2 shows the effect of $A_2P_4$ administration on $Cl^-$ secretion in airway epithelia prestimulated with UTP.

The method of the present invention can be used, to facilitate (i.e., enhance, speed, assist) the clearance of mucous secretions from the lungs of a subject in need of such treatment for any reason, including (but not limited to) retained secretions arising from airway diseases such as cystic fibrosis, chronic bronchitis, asthma, bronchiectasis, post-operative atelectasis (plugging of airways with retained secretions after surgery), and Kartagener's syndrome.

The present invention is concerned primarily with the treatment of human subjects, but may also be employed for the treatment of other mammalian subjects, such as dogs and cats, for veterinary purposes.

Compounds of Formula I and the pharmaceutically acceptable salts thereof (i.e., active compounds) may be prepared in accordance with the techniques described herein and variations thereof which will be apparent to those skilled in the art. As an example, synthesis of UppppU ($U_2P_4$), a known compound, may be carried out by condensation of UDP using the water soluble carboimide EDC (1-ethyl-3-[3-dimethyl-ammonio-propyl]-carboimide hydrochloride). See K. E. Ng and L. E. Orgel, *Nucleic Acids Research* 15, 3572–80 (1987). $U_2P_4$ may also be prepared according to the methods described in C. Vallejo et al., *Biochem. Biophys. Acta* 438, 304–09 (1976).

Amiloride and its use in hydrating lung mucous secretions is known and described in U.S. Pat. No. 4,501,729 to Boucher and Knowles (all patent references recited herein are to be incorporated by reference herein in their entirety). Benzamil (also known as 3,5-diamino-6-chloro-N-(benzylaminoaminomethylene) pyrazinecarboxamide) and phenamil (also known as 3,5-diamino-6-chloro-N-(phenylaminoaminomethylene)pyrazinecarboxamide) are known compounds and are disclosed in U.S. Pat. No. 3,313,813 to E. Cragoe. The terms "benzamil", "phenamil", and "amiloride", as used herein, include the pharmaceutically acceptable salts thereof (i.e., salts as given above), such as (but not limited to) amiloride hydrochloride, benzamil hydrochloride or phenamil hydrochloride.

Active compounds of the present invention may, as noted above, be prepared as pharmaceutically acceptable salts thereof. Pharmaceutically acceptable salts are salts that retain the desired biological activity of the parent compound and do not impart undesired toxicological effects. Examples of such salts are (a) basic salts such as alkali metal salts (e.g., sodium or potassium), alkaline earth metal salts, and ammonium and tetraalkyl ammonium salts (e.g., $NX_4^+$, wherein X is a $C_{1-4}$ alkyl group), and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (c) salts formed from elemental anions such as chlorine, bromine, and iodine.

The active compounds disclosed herein may be administered to the lungs of a subject by any suitable means, but are preferably administered by administering an aerosol suspension of respirable particles comprised of the active compound, which the subject inhales. The respirable particles may be liquid or solid. The active compound can be aerosolized in a variety of forms, such as, but not limited to, dry powder inhalants, metered dose inhalants, or liquid/liquid suspensions. In dry powder delivery, the active compound may be formulated alone or in combination with a diluent or carrier such as a sugar, where the compounds may be intimately incorporated in the matrix through glassification, or simply admixed with the carrier (e.g., lactose, sucrose, trehalose or mannitol) or other acceptable excipients for transport, manufacture, dispersion, or delivery to the lungs or airways.

Aerosols of liquid particles comprising the active compound may be produced by any suitable means, such as with a pressure-driven jet aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic (but which may be hypertonic) with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient. typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 200 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

Any propellant may be used in carrying out the present invention, including both chlorofluorocarbon-containing propellants and non-chlorofluorocarbon-containing propellants. Thus, fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3$—CHF—$CF_2H$; $CF_3$—$CH_2$—$CF_2H$; $CF_3$—CHF—$CF_3$; $CF_3$—$CH_2$—$CF_3$; $CF_3$—CHCl—$CF_2Cl$; $CF_3$—CHCl—$CF_3$; cy—$C(CF_2)_3$—CHCl; $CF_3$—CHCl—$CH_2Cl$; $CF_3$—CHF—$CF_2Cl$; $CF_3$—CHCl—CFHCl; $CF_3$—CFCl—CFHCl; $CF_3$—$CF_2$—$CF_2H$; $CF_3$—$CF_2$—$CH_3$; $CF_2H$—$CF_2$—$CFH_2$; $CF_3$—$CF_2$—$CFH_2$; $CF_3$—$CF_2$—$CH_2Cl$; $CF_2H$—$CF_2$—$CH_3$; $CF_2H$—$CF_2$—$CH_2Cl$; $CF_3$—$CF_2$—$CF_2$—$CH_3$; $CF_3$—$CF_2$—$CF_2$—$CF_2H$; $CF_3$—CHF—CHF—$CF_3$; $CF_3$—O—$CF_3$; $CF_3$—O—$CF_2H$; $CF_2H$—H—O—$CF_2H$; $CF_2H$—O—$CFH_2$; $CF_3$—O—$CH_3$, $CF_3$—O—$CF_2$—$CF_2H$; $CF_3$—O—$CF_2$—O—$CF_3$; cy—$CF_2$—$CF_2$—O—$CF_2$—; cy—CHF—$CF_2$—O—$CF_2$—; cy—$CH_2$—$CF_2$—O—$CF_2$—; cy—$CF_2$-O—$CF_2$—O—$CF_2$—; $CF_3$—O—$CF_2$—Br; $CF_2H$—O—$CF_2$-Br; and mixtures thereof, where "cy" denotes a cyclic compound in which the end terminal covalent bonds of the structures shown are the same so that the end terminal groups are covalently bonded together. Particularly preferred are hydrofluoroalkanes such as 1,1,1,2-tetrafluoroethane (propellant 134a) and heptafluoropropane (propellant 227). A stabilizer such as a fluoropolymer may optionally be included in formulations of fluorocarbon propellants, such as described in U.S. Pat. No. 5,376,359 to Johnson.

Figure 3:
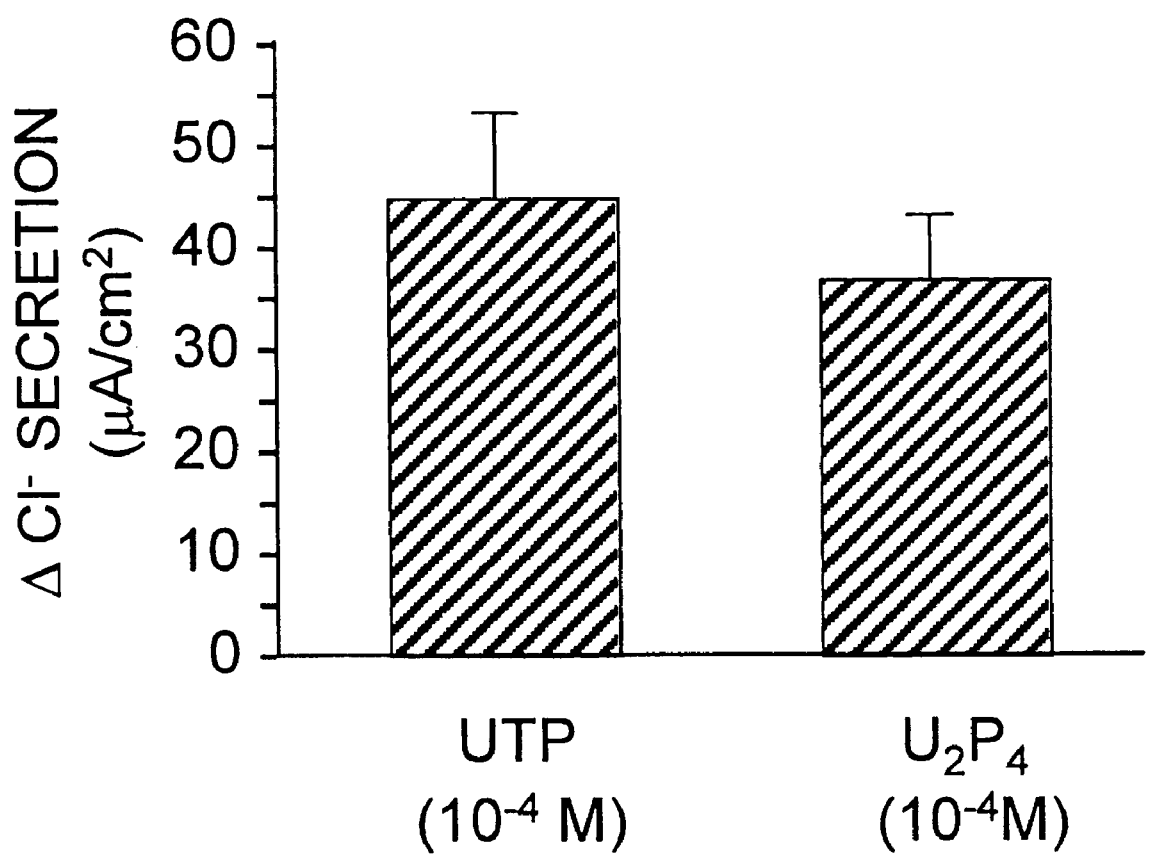
FIG. 3 shows a comparison of the maximal efficacy of UTP and $U_2P_4$ on $Cl^-$ secretion by cultured human nasal epithelial (HNE) monolayers. The data shown in this Figure illustrate the maximal $Cl^-$ secretory rate in $\mu A/cm^2$ as mean values±SEM, of n=5 or more per drug group.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The dosage of the compound of Formula I, or pharmaceutically acceptable salt thereof, will vary depending on the condition being treated and the state of the subject, but generally may be a therapeutically effective amount sufficient to treat the presenting lung condition of a patient in need of such treatment (for example, a localized concentration reaching the lung surface from about $10^{-9}$ to about $10^{-1}$ moles/liter). Depending upon the solubility of the particular formulation of active compound administered, the daily dose may be divided among one or several unit dose administrations. Amiloride, benzamil or phenamil administered concurrently with the compound of Formula I or salt thereof may be given in the same dosages as the compound of Formula I or salt thereof.

Solid or liquid particulate pharmaceutical formulations containing active agents of the present: invention should include particles of respirable size: that is, particles of a size sufficiently small to pass through the mouth and larynx upon inhalation and into the bronchi and alveoli of the lungs. In general, particle size should be within a range suitable for depositing a therapeutically effective amount in the lungs or in the airways, for example, about 1–10 microns, to treat the lung condition of a patient in need of such treatment. Particles of non-respirable size which are included in the aerosol tend to be deposited in the throat and swallowed, and the quantity of non-respirable particles in the aerosol is preferably minimized. For nasal administration, a particle size in the range of 10–500 microns is preferred to ensure retention in the nasal cavity.

In the manufacture of a formulation according to the invention, active agents or the physiologically acceptable salts or free bases thereof are typically admixed with, inter alia, an acceptable carrier. rhe carrier must, of course, be acceptable in the sense of being compatible with any other ingredients in the formulation and must not be deleterious to the patient. The carrier may be a solid or a liquid, or both, and is preferably formulated with the compound as a unit-dose formulation, which may contain from 0.1% to 99% by weight of the active compound. One or more active compounds may be incorporated in the formulations of the invention, which formulations may be prepared by any of the well-known techniques of pharmacy consisting essentially of admixing the components.

Compositions containing respirable dry particles of active compound may be prepared by grinding the active compound with a mortar and pestle, and then passing the micronized composition through a 400 mesh screen to break up or separate out large agglomerates.

Amiloride, benzamil or phenamil used to prepare compositions for the present invention may alternatively be in the form of a pharmaceutically acceptable free base of benzamil or phenamil. Because the free base of the compound is less soluble than the salt, free base compositions are employed to provide more sustained release of benzamil or phenamil to the lungs. Amiloride, benzamil or phenamil present in the lungs in particulate form which has not gone into solution is not available to induce a physiological response, but serves as a depot of bioavailable drug which gradually goes into solution.

The pharmaceutical composition may optionally be combined with a carrier to aid in dispersion or transport. A suitable carrier such as a sugar (e.g., lactose, sucrose, trehalose, mannitol) may be blended with the active compound in any suitable ratio (e.g., a 1 to 1 ratio by weight).

The present invention is explained in greater detail in the following non-limiting Examples.

EXAMPLE 1

Effect of Dinucleotide A,L on Chloride ($Cl^-$) Secretion

Normal airway cells were cultured on permeable supports and $Cl^-$ secretion assayed as previously described in M. J. Stutts, et al., *Am. J. Physiol.* 267, C1442–C1451 (1994). $Cl^-$ secretion was measured after administration of the dinucleotide $A_2P_4$ (Sigma Chemicals, St. Louis, Mo.). Amiloride was added to block airway epithelial sodium absorption. $A_2P_4$ had little effect when exposed to the basolateral surface of the airway epithelial preparation, but on the luminal surface stimulated additional $Cl^-$ secretion in airway epithelia that had been treated with forskolin. This result is shown in FIG. 1. Because forskolin maximally activates the CFTR-mediated cAMP-regulated $Cl^-$channels of airway epithelia, this result suggests that $A_2P_4$ stimulates luminal purinergic $P_{2U}$ receptors.

Moreover, the administration of $A_2P4$ had no effect on $Cl^-$ secretion in airway epithelia pre-stimulated with UTP, which is known to activate non-CFTR $Cl^-$ channels. These results, shown in FIG. 2, suggest regulation by $A_2P_4$ of the non—CFTR $Cl^-$ channel that is controlled by purinergic receptors and further suggests that $A_2P_4$ stimulates the same airway epithelial $Cl^-$ channels as UTP acting through $P_{2U}$ receptors. Stimulation of this receptor is thus a therapeutic strategy for certain lung diseases, including cystic fibrosis.

EXAMPLE 2

Effect of Dinucleotide $U_2P_4$ on Chloride ($Cl^-$) Secretion

Studies were carried out according to the method described in Example 1 to compare the effectiveness (efficacy) of UTP and $U_2P_4$. Cultured airway epithelia were exposed to a concentration of from $10^{-9}$ M to $10^{-3}$ M of either UTP or $U_2P_4$ in 6 ml of solution circulating over the mucosal surface. The tissues were pretreated with amiloride ($10^{-4}$ M) to block $Na^+$ absorption. Under these conditions, the current generated by the tissues is due to $Cl^-$ secretion. UTP and $U_2P_4$ induced a similar pattern of $Cl^-$ secretion. At $10^{-4}$ M, the highest concentration tested, UTP and $U_2P_4$ were equieffective (equiefficacious). The Table provided below indicates that there is no difference in the magnitude of $Cl^-$ secretion induced by $10^{-4}$ M UTP and $10^{-4}$ M $U_2P_4$.

| | UTP | $U_2P_4$ |
|---|---|---|
| Mean $Cl^-$ secretion Induced ($\mu A/cm^2$) | 45.3 | 43.8 |
| Variance | 221.0 | 155.3 |
| Observations | 11 | 8 |
| Pooled Variance | 194.0 | |
| Hypothesized Mean Difference | 0 | |
| df | 17 | |
| t Stat | 0.223 | |
| P(T<=t) one-tail | 0.413 | |
| t Critical one-tail | 1.739 | |
| P(T<=t) two-tail | 0.826 | |
| t Critical two-tail | 2.109 | |

EXAMPLE 3

Effect of $U_2P_4$on Maximum Chloride ($Cl^-$) Secretion Rate

FIG. 3 illustrates a comparison of the maximal efficacy of UTP and $U_2P_4$ on $Cl^-$ secretion by cultured human nasal epithelial (HNE) monolayers. Cells were dissociated from freshly excised human nasal turbinate specimens using the protease XIV technique that has been previously reported. See J. R. Yankaskas et al., *Am. Retv. Respir. Dis.* 132 (6), 1281–1287 (1985). Cells were then plated at high density on collagen matrix supports (CMS) that permit the growth and polarization of epithelial monolayers utilizing serum-free, hormone-supplemented medium and an air-liquid interface (ALI) culture system. After achieving a maximal transepithelial potential difference, typically on Day 7 after seeding, the CMS's were mounted in miniaturized Ussing chambers, bathed in bilateral Cl⁻-free solutions, Na⁺ transport inhibited by the application of amiloride ($10^{-4}$ M) to the luminal bathing solution, and the effect of the mucosal addition of UTP ($10^{-4}$ M) or $U_2P_4$ ($10^{-4}$ M) measured. The data shown in FIG. 3 depict the maximal Cl⁻ secretory rate in $\mu A/cm^2$ as mean value±SEM, of n=5 or more per drug group.

The foregoing Examples are illustrative of the present invention, and are not to be construed as limiting thereof. The invention is defined by the following claims, with equivalents of the claims to be included therein.

That which is claimed is:

1. A pharmaceutical formulation comprising, in an amount effective to hydrate lung mucous secretions, and in a pharmaceutically acceptable carrier, a compound of Formula (I):

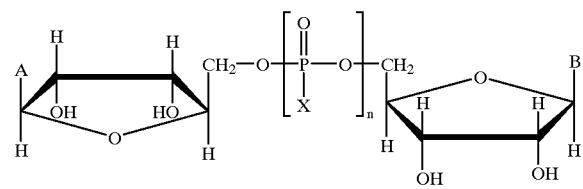

(I)

wherein:

n is from 1 to 6;

X is —OH or —SH;

and A and B are each independently selected from the group consisting of:

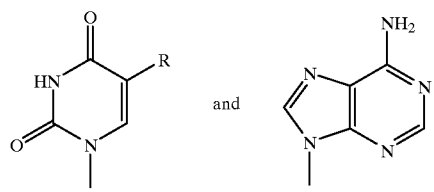

wherein R is H or Br;

or a pharmaceutically acceptable salt thereof.

2. A pharmaceutical formulation according to claim 1, further comprising a compound selected from the group consisting of amiloride, benzamil and phenamil, or a pharmaceutically acceptable salt thereof.

3. A pharmaceutical formulation according to claim 1, wherein said carrier is a liquid carrier.

4. A pharmaceutical formulation according to claim 1, wherein said carrier is a solid particulate carrier.

5. A method of hydrating mucous secretions in the lungs of a subject in need of such treatment, comprising administering to the lungs of the subject a compound of Formula I below, or a pharmaceutically acceptable salt thereof, in an amount effective to hydrate lung mucous secretions:

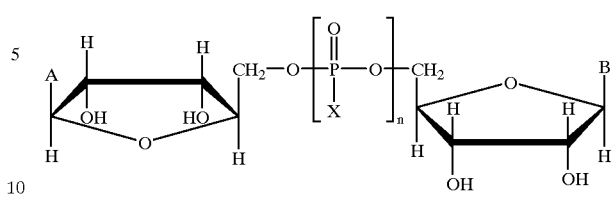

(I)

wherein:

n is from 1 to 6;

X is —OH or —SH;

and A and B are each independently selected from the group consisting of:

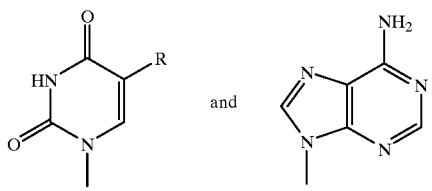

wherein R is H or Br.

6. A method according to claim 5, wherein said compound is delivered by administering an aerosol suspension of respirable particles comprised of said compound to the lungs of said subject.

7. A method according to claim 6, wherein said particles are selected from the group consisting of solid particles and liquid particles.

8. A method according to claim 5, further comprising concurrently administering a compound selected from the group consisting of amiloride, benzamil and phenamil to said subject in an amount effective to inhibit the reabsorption of water from lung mucous secretions.

9. A method of treating cystic fibrosis in a human subject in need of such treatment, comprising administering by inhalation an aerosol suspension of respirable particles to the respiratory system of said subject, said particles comprised of a compound of Formula I below, or a pharmaceutically acceptable salt thereof:

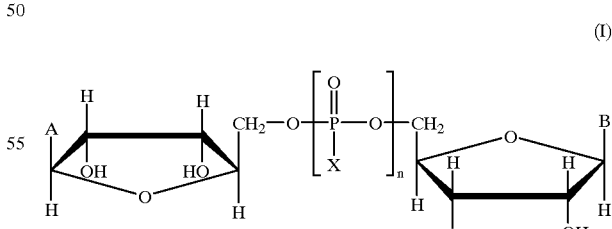

(I)

wherein:

n is from 1 to 6;

X is —OH or —SH;

and A and B are each independently selected from the group consisting of:

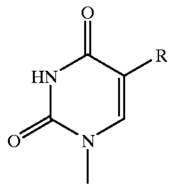

and

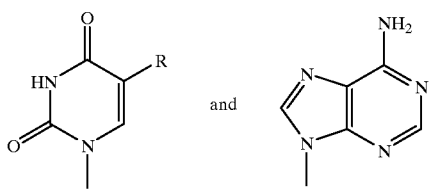
wherein R is H or Br;
in an amount effective to hydrate retained lung mucous secretions in the lungs of said subject, whereby the retained mucous secretions are more easily transported from the lungs via mucociliary action.

10. A method according to claim 9, wherein said compound is delivered by administering an aerosol suspension of respirable particles comprised of said compound to the lungs of said subject.

11. A method according to claim 9, wherein said particles are selected from the group consisting of solid particles and liquid particles.

12. A method according to claim 9, further comprising concurrently administering a compound selected from the group consisting of amiloride, benzamil and phenamil to said subject in an amount effective to inhibit the reabsorption of water from lung mucous secretions.

13. A method of hydrating mucous secretions :in the lungs of a subject in need of such treatment, comprising administering to the lungs of the subject a compound of Formula I below, or a pharmaceutically acceptable salt thereof, in an amount effective to hydrate lung mucous secretions:

(I)

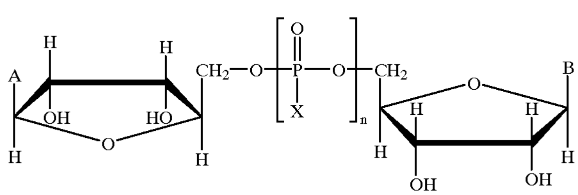

wherein:

A and B are each 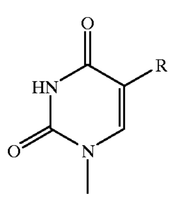 n is 4;

X is —OH; and

R is H.

14. A method according to claim 13, wherein said compound is delivered by administering an aerosol suspension of respirable particles comprised of said compound to the lungs of said subject.

15. A method according to claim 13, wherein said particles are selected from the group consisting of solid particles and liquid particles.

16. A method according to claim 13, further comprising concurrently administering a compound selected from the group consisting of amiloride, benzamil and phenamil to said subject in an amount effective to inhibit the reabsorption of water from lung mucous secretions.

17. A method of treating cystic fibrosis in a human subject in need of such treatment, comprising administering by inhalation an aerosol suspension of respirable particles to the respiratory system of said subject, said particles comprised of a compound of Formula I below, or a pharmaceutically acceptable salt thereof:

(I)

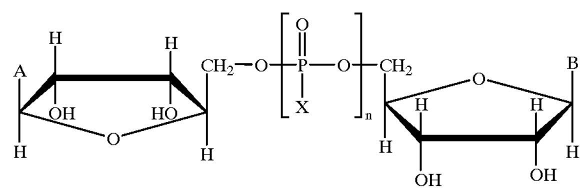

wherein:

A and B are each 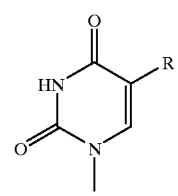 n is 4;

X is —OH; and

R is H.

18. A method according to claim 17, wherein said compound is delivered by administering an aerosol suspension of respirable particles comprised of said compound to the lungs of said subject.

19. A method according to claim 18, wherein said particles are selected from the group consisting of solid particles and liquid particles.

20. A method according to claim 17, further comprising concurrently administering a compound selected from the group consisting of amiloride, benzamil and phenamil to said subject in an amount effective to inhibit the reabsorption of water from lung mucous secretions.

* * * * *